United States Patent [19]

Kaeding

[11] Patent Number: 4,929,791
[45] Date of Patent: May 29, 1990

[54] CATALYTIC CONVERSION OF PROPANE TO ETHYLENE OVER ZSM-50

[75] Inventor: Warren W. Kaeding, Lawrenceville, N.J.

[73] Assignee: Mobil Oil Corporation, New York, N.Y.

[21] Appl. No.: 217,111

[22] Filed: Jul. 7, 1988

Related U.S. Application Data

[63] Continuation of Ser. No. 784,967, Oct. 7, 1985, abandoned.

[51] Int. Cl.$^5$ .............................................. C07C 4/06
[52] U.S. Cl. .................................. 585/651; 585/648; 585/649
[58] Field of Search ............... 585/650, 651, 648, 649, 585/DIG. ZSM

[56] References Cited

U.S. PATENT DOCUMENTS

| | | | |
|---|---|---|---|
| 3,668,268 | 6/1972 | Mulaskey | 260/676 |
| 3,668,269 | 6/1972 | Chloupek | 260/676 R |
| 3,760,024 | 9/1973 | Cattanach | 260/673 |
| 3,812,199 | 5/1974 | Chen et al. | 260/676 R |
| 3,972,832 | 8/1976 | Butter et al. | 252/437 |
| 4,287,166 | 9/1981 | Dwyer et al. | 423/329 |
| 4,296,083 | 10/1981 | Rollmann | 423/329 |
| 4,537,754 | 8/1985 | Casci et al. | 502/77 |
| 4,547,618 | 10/1985 | Forbus | 585/660 |
| 4,554,260 | 11/1985 | Pieters et al. | 502/61 |
| 4,665,251 | 5/1987 | Chu | 585/415 |
| 4,686,316 | 8/1987 | Morrison | 585/708 |

FOREIGN PATENT DOCUMENTS

| | | | |
|---|---|---|---|
| 0042226 | 12/1981 | European Pat. Off. | 423/326 |
| 0051318 | 5/1982 | European Pat. Off. | 423/328 |
| 0170486 | 2/1986 | European Pat. Off. | |
| 0174121 | 3/1986 | European Pat. Off. | |
| 1563345 | 3/1980 | United Kingdom | |

OTHER PUBLICATIONS

*Applied Catalysis*, 19 (1985) 153–163, "Reactions of Propane over a Bifunctional Pt/H–ZSM-5 Catalyst."

*Primary Examiner*—Asok Pal
*Attorney, Agent, or Firm*—A. J. McKillop; C. J. Speciale; Edward F. Kenehan, Jr.

[57] ABSTRACT

There is provided a process for converting propane to ethylene over a zeolite catalyst comprising ZSM-50. This zeolite may be contacted with an anhydrous acidic oxide gas capable of accepting hydrogen by reacting therewith, such as sulfur dioxide ($SO_2$), in order to enhance the ethylene selectivity of the conversion. The zeolite may either be pretreated with this acidic oxide gas or contacted in situ by cofeeding the acidic oxide gas along with the propane reactant. Particularly in view of the tendency of zeolites such as ZSM-5 to further convert olefins produced into aromatics and other hydrocarbons, the large degree of ethylene selectivity achieved by the process of the present invention is surprising.

7 Claims, No Drawings

CATALYTIC CONVERSION OF PROPANE TO ETHYLENE OVER ZSM-50

This is a continuation of copending application Ser. No. 784,967, filed on Oct. 7, 1985, now abandoned.

CROSS-REFERENCE TO RELATED APPLICATIONS

This application is related to copending U.S. application Ser. No. 642,961, filed Aug. 21, 1984, which discloses the conversion of propane to light olefins and aromatics over a zeolite designated as ZSM-57.

This application is also related to copending U.S. application Ser. No 784,966, filed Oct. 7, 1985, which discloses the conversion of propane to ethylene over ZSM-23.

The entire disclosures of these cross-referenced applications are expressly incorporated herein by reference.

BACKGROUND

Ethylene is prepared commercially by heating ethane, propane, higher paraffins or naphtha, diluted with steam, at about 850° C., 1550° F., for very short contact times, without a catalyst. Highest ultimate yields come from ethane (81%), propane (43%) and n-butane (41.5%). All world-scale plants with billion-pound-per-year ethylene capacity are based on this thermal cracking/dehydrogenation technology. Although a host of rival schemes has been studied, none have reached commercial application.

Weaknesses in the established process are (1) high reaction temperature and low hydrocarbon partial pressure, (2) low product separation/purification temperatures ($-150°$ to $-200°$ F.) and high pressure (500 psig), (3) relatively low yields from $C_3$ and higher feeds, (4) a complex mixture of products, and (5) relatively high capital and operating costs.

Olefins have been prepared from methanol over ZSM-5 with low activity, $SiO_2/Al_2O_3$ 300/1, M. M. Wu and W. W. Kaeding, J. Cat. 88 478 (1984). In the majuor $C_2$–$C_4$ olefins product, ethylene is usually the smallest component (10–15 wt %). When n-butane was used with these same catalysts, propylene and $C_5+$ olefins were produced with only traces of ethylene. When propane is converted over catalysts with various oxides on silica or alumina such as chromium oxide, propylene is the major product.

SUMMARY

According to one aspect of the invention, there is provided a process for converting propane to ethylene, said process comprising contacting said propane with a catalyst comprising ZSM-50 under sufficient conversion conditions.

ZSM-50 is described in U.S. Application Ser. No. 705,822, filed Feb. 26, 1985, the entire disclosure of which is expressly incorporated herein by reference.

ZSM-50 may have a formula, in terms of moles of oxides per 100 moles of silica on an anhydrous basis, as follows:

$$(0-10)M_{2/n}O:(1-5)Al_2O_3:(100)SiO_2$$

wherein M is at least one cation having a valence n. ZSM50 is characterized by a distinctive X-ray diffraction pattern substantially as shown in Table 1.

TABLE 1

| Interplanar d-Spacing (A) | Relative Intensity, $I/I_o$ |
|---|---|
| 20.1 ± .3 | W |
| 11.1 ± .17 | S |
| 10.1 ± .16 | M |
| 9.7 ± .14 | W |
| 5.77 ± .09 | W |
| 5.61 ± .09 | W |
| 4.64 ± .07 | M |
| 4.35 ± .07 | M |
| 4.30 ± .07 | VS |
| 4.00 ± .06 | S |
| 3.85 ± .06 | M |
| 3.70 ± .06 | M |
| 3.42 ± .05 | W |
| 3.35 ± .05 | W |
| 3.27 ± .05 | M |
| 3.24 ± .05 | W |
| 2.94 ± .04 | W |
| 2.53 ± .04 | W |

These values were determined by standard techniques. the radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Table 1, the relative intensities are given in terms of the symbols W=weak, M=medium, S=strong and VS=very strong. in terms of intensities, these may be generally designated as follows:

W=0–20
M=20–40
S=40–60
VS=60–100

In an as-synthesized form, zeolite ZSM-50 has a formula, on an anhydrous hasis and in terms of moles or oxides per 100 moles of silica, as follows:

$$(0-4)R_2O:(\ \ )-10)M_{2/n}O:(1-5\_Al_2O_3:(100)SiO_2$$

wherein M is an alkali or alkaline earth metal, n is the valence of M, and R is an organic cation of diquaternary directing agent compound generally expressed by the following formula:

$$X(CH_3)_3N(CH_3)_3X$$

wherein X is an anion, e.g. halide, such as iodide.

ZSM-50 can be prepared from a reaction mixture containing sources of an alkali or alkaline earth metaloxide, an oxide of aluminum, an oxide of silicon, an organic cation and water and having a composition, in terms of mole ratios of oxides, within the following ranges:

| Reactants | Useful | Preferred |
|---|---|---|
| $SiO_2/Al_2O_3$ | 20–100 | 30–90 |
| $OH^-/SiO_2$ | 0.1–0.6 | 0.1–0.3 |
| $R/SiO_2$ | 0.05–0.6 | 0.1–0.3 |
| $M/SiO_2$ | 0.01–1.0 | 0.1–0.6 | wherein M is an alkali or alkaline earth metal and R is an organic cation derived from the above identified diquaternary directing agent compound.

Crystallization of conventional zeolite ZSM-50 can be carried out at either static or stirred condition in a suitable reactor vessel, such as for example, polypropylene jars or teflon lined or stainless steel authclaves. The total useful range of temperatures for crystallization is from about 100° C. to about 200° C. for a time of about 48 hours to about 15 days. Thereafter, the crystals are separated from the liquid and recovered.

In accordance with the present invention, the zeolite catalyst may be contacted with an anhydrous acidic oxide gas capable of accepting hydrogen by reacting therewith. Examples of such gases include oxidative dehydrogenation agents such as sulfur dioxide ($SO_2$) and nitrous oxide ($N_2O$). Such oxide gases may be contacted with the zeolites by a pretreatment procedure, e.g., prior to any catalytic use, or as a cofeed with the propane reactant.

The zeolites suitable for use in accordance with the present invention may be combined with another material resistant to the temperatures and other conditions employed in the present organic conversion process. Such matrix materials include active and inactive materials and synthetic or naturally occurring zeolites as well as inorganic materials such as clays, silica and/or metal oxides, e.g. alumina. The latter may be either naturally occurring or in the form of gelatinous precipitates, sols or gels including mixtures of silica and metal oxides. Use of a material in conjunction with the zeolite, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline silicate materials have been incorporated into naturally occurring clays, e.g. bentonite and kaolin. These materials, i.e. clays, oxides, etc., function, in part, as binders for the catalyst. It is desirable to provide a catalyst having good crush strength, because in use the catalyst may be subjected to rough handling, which tends to break the catalyst down into powder-like materials which cause problems in processing.

Naturally occurring clays which can be composited with the zeolite include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolite catalyst hereby synthesized can be composited with a porous matrix material such as silica-alumina, silica-magnesia, silica-zirconia, silica-thoria, silica-beryllia, silica-titania, as well as ternary compositions such as silica-alumina-thoria, silica.alumina.zirconia, silica.alumina.magnesia and silica-magnesia-zirconia. The matrix can be in the form of a cogel. A mixture of these components could also be used. The relative proportions of finely divided crystalline silicate and matrix vary widely with the crystalline silicate content ranging from about 1 to about 90 percent by weight, and more usually in the range of about 2 to about 90 percent by weight of the composite.

Conditions for converting propane in accordance with the present invention may include a temperature of from about 100° C. to about 700° C., a pressure of from about 0.1 atmosphere to about 60 atmospheres, and a weight hourly space velocity of from about 0.5 to about 400. The feedstock, in addition to propane, may optionally comprise, e.g., up to about 98% of a diluent gas, especially an inert diluent gas. The feedstock may also comprise a small percentage, e.g., 1 percent by weight or less, of impurities associated with propane feedstocks such as butane.

Although ZSM-50 has been found to be particularly suited for converting propane to ethylene in accordance with the present invention, it is possible that other molecular sieve catalysts may also be suitable for this purpose.

EXAMPLE 1

High silica ZSM-50 sample was synthesized with dibenzyldimethylammonium chloride according to procedures outlined by Rubin in the aforementioned U.S. application Ser. No. 705,822, filed Feb. 6, 1985. The product was filtered, water-washed and dried at 120° C. X-ray diffraction shows a highly crystalline ZSM-50. Compositional data are, wt %:

| | |
|---|---|
| $SiO_2$ | 80.4 |
| $Al_2O_3$ | 0.65 |
| N | 0.63 |
| Na | 0.57 |
| Ash | 86.16 |
| $SiO_2/Al_2O_3$ | 210 molar ratio |

Low silica ZSM-50 was prepared with Diquat-6 bromide [$Br(CH_3)_3N(CH_2)_6N(CH_3)_3Br$] according to the method of Valyocsik in U.S. Application Ser. No. 386,456, filed June 8, 1982.

The mixture was crystallized, with stirring, at 160° C. for 4 days. The product was 90% crystalline ZSM-50. Compositional data are, wt %:

| | |
|---|---|
| $SiO_2$ | 83.0 |
| $Al_2O_3$ | 3.6 |
| N | 1.29 |
| Na | 0.27 |
| Ash | 86.38 |
| $SiO_2/Al_2O_3$ | 39.2 molar ratio |

Both preparations were converted to the ammonium form by a preliminary calcination at 500° C. in $N_2$ followed by air. They were then treated with 10% $NH_4Cl$ solution.

In Examples which follow, ZSM-50 samples of Example 8 were used to convert propane. Reagent grade propane containing 0.9% n-butane was used without further purification. Corrections were made for the butane in runs with low conversion. Pive to ten grams of catalyst wafers, crushed and screened to 14-20 mesh were used in glass screening reactors. Effluent gas was sampled in a hot syringe and analyzed for hydrocarbons. A second sample was analyzed with an argon carrier gas to measure hydrogen. Material balances of ±5% were usually obtained.

When sulfur dioxide was used, it was used in accordance with the following procedure:

A. Sulfur dioxide, 20 cc/min, was passed over the catalyst for 30–60 min at 300° C., followed by calcination in air for 30–60 min at 500° C.

B. After treatment of the catalyst as described in A, above, 1-3 wt % $SO_2$ was added to the propane feed for the screening reaction.

Screening tests at various temperatures (400°-650° C.) and weight hourly space velocities (WHSV) ranging from 0.86 to 6.9 were used with propane. In addition, sulfur dioxide (1-5%) was used to modify the catalyst and/or as a hydrogen acceptor. Ideally, it would aid dehydrogenation of propane, Eq. 1, by consuming hydrogen thereby preventing the reverse reaction, Eq. 2. Higher conversions to Dehydrogenation

$$CH_3CH_2CH_3 \rightleftharpoons CH_3CH=CH_2 + H_2 \quad (1)$$

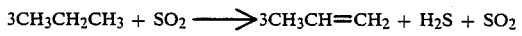
$$3CH_3CH_2CH_3 + SO_2 \longrightarrow 3CH_3CH=CH_2 + H_2S + SO_2 \quad (2)$$

Cracking

$$CH_3CH_2CH_3 \longrightarrow CH_2=CH_2 + CH_4 \quad (3)$$

Objective

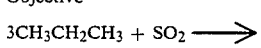
$$3CH_3CH_2CH_3 + SO_2 \longrightarrow \quad (4)$$

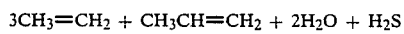
$$3CH_3=CH_2 + CH_3CH=CH_2 + 2H_2O + H_2S$$

propylene should occur. The well-known propane cracking reaction, Eq. 3, occurs and is interesting because the desired ethylene is a product. A catalyst and hydrogen acceptor that would reduce methane formation and increase ethylene yield, Eq. 4, is a desirable objective.

EXAMPLE 2

The HZSM-50 sample having a $SiO_2/Al_2O_3$ molar ratio of 200/1 was used to convert propane.

Screening results for propane are summarized in Table 2. Conversion increased significantly with increases in temperature and contact time. The highest ethylene selectivity observed was 35%, Run 7. Significant amounts of propylene (15-20% selectivity) and methane (22-29%) were also obtained.

Catalytic amounts (1%) of sulfur dioxide and nitrous oxide were added to the propane feed streams to determine whether olefin yield could be increased. Results are summarized in Table 3. In almost every case, a small increase in ethylene selectivity was observed.

TABLE 2

| | Conversion of Propane over HZSM-50, $SiO_2/Al_2O_3$ = 210/1 | | | | | | | | |
|---|---|---|---|---|---|---|---|---|---|
| Run No. | 1 | 2 | 3 | 4 | 5 | 6 | 7 | 8 | 9 |
| Temp. °C. | 550 | 550 | 550 | 600 | 600 | 600 | 650 | 650 | 650 |
| WHSV $C_3H_8$ | 3.46 | 1.73 | .864 | 3.46 | 1.73 | .864 | 3.46 | 1.73 | .864 |
| Conversion | 6 | 10 | 14 | 19 | 28 | 40 | 41 | 53 | 73 |
| Selectivity, wt. % | | | | | | | | | |
| $BTX^{(a)}$ | 0 | .6 | 2.8 | 3.1 | 5.0 | 10.5 | 5.6 | 11.8 | 15.2 |
| $C_9+$ | 0 | 9.0 | 1.0 | 5.1 | 1.7 | 3.7 | .9 | 2.6 | 4.8 |
| Tot. Liq. Prod. | 0 | 9.6 | 3.8 | 8.2 | 6.7 | 14.2 | 6.5 | 14.4 | 20.0 |
| $H_2$ | .7 | .5 | .6 | .9 | 1.0 | 1.0 | 1.4 | 1.5 | 1.9 |
| $CO/CO_2$ | 0 | 0 | 0 | 0 | 0 | 0 | 0 | 0 | 0 |
| $CH_4$ | 22.3 | 22.6 | 25.6 | 24.2 | 26.1 | 27.0 | 26.6 | 26.4 | 29.5 |
| $C_2H_6$ | 2.8 | 5.1 | 7.8 | 4.4 | 6.5 | 8.4 | 5.3 | 6.8 | 8.9 |
| $C_2H_4$ | 31.8 | 28.2 | 24.1 | 32.3 | 28.6 | 21.0 | 34.6 | 27.0 | 21.3 |
| $C_3H_8$ | $SM^{(b)}$ | SM | SM | SM | SM | SM | SM | SM | SM |
| $C_3H_6$ | 17.5 | 17.1 | 18.1 | 19.9 | 19.1 | 16.0 | 20.5 | 16.8 | 12.8 |
| $C_4H_{10}$ | 24.9 | 12.3 | 12.8 | 5.2 | 5.0 | 5.6 | .6 | 1.5 | 1.2 |
| $C_4H_8$ | 0 | 4.6 | 7.2 | 4.9 | 7.0 | 6.8 | 4.5 | 5.6 | 4.4 |
| $C_2-C_4$ | 27.7 | 17.4 | 20.6 | 9.6 | 11.5 | 14.0 | 5.9 | 8.3 | 10.1 |
| | 49.3 | 49.9 | 49.4 | 57.1 | 54.7 | 43.8 | 59.6 | 49.4 | 38.5 |
| Total | 100.0 | 100.0 | 100.0 | 100.0 | 100.0 | 100.0 | 100.0 | 100.0 | 100.0 |

$^{(a)}$Benzene, toluene, xylene.
$^{(b)}$SM = starting material.

TABLE 3

| | Conversion of Propane over HZSM-50, $SiO_2/Al_2O_3$ = 210/1 with $SO_2$ | | | | | |
|---|---|---|---|---|---|---|
| Run No. | 10 | 11 | 12 | 13 | 14 | 15 |
| Temp. °C. | 600 | 600 | 600 | 650 | 650 | 650 |
| WHSV $C_3H_8$ | 3.46 | 1.73 | .864 | 3.64 | 1.73 | .864 |
| $SO_2$ | .005 | .005 | .005 | .005 | .005 | .005 |
| Conversion | 20 | 26 | 41 | 42 | 57 | 73 |
| Selectivity, wt. % | | | | | | |
| BTX | 1.5 | 4.3 | 11.2 | 4.4 | 10.9 | 17.7 |
| $C_9+$ | 1.5 | 1.1 | 6.3 | .4 | 3.5 | 5.9 |
| Tot. Liq. Prod. | 3.0 | 5.4 | 17.5 | 4.8 | 14.4 | 23.6 |
| $H_2$ | .7 | .8 | 1.0 | 1.1 | 1.2 | 1.5 |
| $CO/CO_2$ | 0 | .2 | .3 | 0 | .1 | .2 |
| $CH_4$ | 26.4 | 26.7 | 26.0 | 27.2 | 26.8 | 27.5 |
| $C_2H_6$ | 4.4 | 6.5 | 8.6 | 5.1 | 6.7 | 8.9 |
| $C_2H_4$ | 35.4 | 29.7 | 20.2 | 34.5 | 27.4 | 20.7 |
| $C_3H_8$ | SM | SM | SM | SM | SM | SM |
| $C_3H_6$ | 19.8 | 19.2 | 15.3 | 20.1 | 16.8 | 12.6 |
| $C_4H_{10}$ | 5.8 | 5.2 | 5.5 | 1.5 | 1.3 | 1.1 |
| $C_4H_8$ | 4.5 | 6.3 | 5.6 | 5.7 | 5.4 | 3.9 |
| Total | 100.0 | 100.0 | 100.0 | 100.0 | 100.0 | 100.0 |

EXAMPLE 3

In a manner similar to Example 2, the more active catalyst of Example 1, containing higher concentrations of aluminum ($SiO_2/Al_2O_3=39$) was tested. Results are summarized in Table 4. In comparison with the previous run ($SiO_2/Al_2O_3=210$), modest increases in conversion were observed. However, the amount of ethylene and total $C_2-C_4$ olefins was relatively low. By doubling the space velocity, Runs 5-8, Table 4, olefin selectivity increased at the expense of lower conversion.

The amount of sulfur dioxide in the feed stream was increased about 20 fold, compared with Example 2, to determine whether it was reacting with propane to remove hydrogen, Eqs. 2 and 4. Significant and encouraging increases in ethylene and propylene selectivities were observed, Table 5, Runs 12, 16. Some elemental sulfur appeared to be present in the product. It was removed by passing the gas stream through alumina at low temperature.

TABLE 4

| | HZSM-50, $SiO_2/Al_2O_3$ = 39/1 | | | | | | | |
| | Propane | | | | | | | |
| Run No. | 1 | 2 | 3 | 4 | 5 | 6 | 7 | 8 |
| --- | --- | --- | --- | --- | --- | --- | --- | --- |
| Temp. °C. | 500 | 550 | 600 | 650 | 500 | 550 | 600 | 650 |
| WHSV $C_3H_8$ | 3.5 | 3.5 | 3.5 | 3.5 | 6.9 | 6.9 | 6.9 | 6.9 |
| Conversion | 15 | 28 | 46 | 47 | 9 | 20 | 35 | 31 |
| Selectivity, wt. % | | | | | | | | |
| BTX | 4.1 | 10.2 | 11.8 | 13.8 | 2.7 | 6.7 | 11.4 | 10.0 |
| $C_9+$ | 1.0 | 2.3 | 3.1 | 2.8 | 11.0 | 2.5 | 2.0 | 2.3 |
| Tot. Liq. Prod. | 5.1 | 12.5 | 14.9 | 16.6 | 13.7 | 9.2 | 13.4 | 12.3 |
| $H_2$ | .6 | 1.1 | 1.8 | 2.3 | .6 | 1.1 | 1.6 | 1.9 |
| $CO/CO_2$ | 0 | 0 | 0 | 0 | 0 | 0 | 0 | 0 |
| $CH_4$ | 15.8 | 23.1 | 28.2 | 26.0 | 14.2 | 21.9 | 25.0 | 24.2 |
| $C_2H_6$ | 8.9 | 12.2 | 11.7 | 7.7 | 5.4 | 8.7 | 7.9 | 5.6 |
| $C_2H_4$ | 8.5 | 12.8 | 18.2 | 23.4 | 12.6 | 18.3 | 23.2 | 27.8 |
| $C_3H_8$ | SM | SM | SM | SM | SM | SM | SM | SM |
| $C_3H_6$ | 9.5 | 12.1 | 13.6 | 16.8 | 13.8 | 16.5 | 17.6 | 12.1 |
| $C_4H_{10}$ | 44.6 | 20.7 | 6.3 | 3.0 | 36.0 | 18.1 | 5.5 | 2.4 |
| $C_4H_8$ | 7.0 | 5.5 | 5.3 | 4.2 | 3.7 | 6.2 | 5.8 | 4.7 |
| Total | 100.0 | 100.0 | 100.0 | 100.0 | 100.0 | 100.0 | 100.0 | 100.0 |

TABLE 5

| | HZSM-50, $SiO_2/Al_2O_3$ = 39/1 | | | | | | | |
| | Propane | | | | | | | |
| Run No. | 9 | 10 | 11 | 12 | 13 | 14 | 15 | 16 |
| --- | --- | --- | --- | --- | --- | --- | --- | --- |
| Temp. °C. | 500 | 550 | 600 | 650 | 500 | 550 | 600 | 650 |
| WHSV $C_3H_8$ | 6.91 | 6.91 | 6.91 | 6.91 | 3.46 | 3.46 | 3.46 | 3.46 |
| $SO_2$ | .105 | .105 | .105 | .105 | .105 | .105 | .105 | .105 |
| Conversion | 10 | 13 | 18 | 29 | 10 | 14 | 28 | 50 |
| Selectivity, wt. % | | | | | | | | |
| BTX | 5.7 | 3.9 | 3.2 | 3.1 | 5.7 | 4.8 | 5.8 | 8.1 |
| $C_9+$ | 4.4 | 2.7 | 1.5 | .7 | 3.2 | 1.4 | 1.8 | 1.7 |
| Tot. Liq. Prod. | 10.1 | 6.6 | 4.7 | 3.8 | 8.9 | 6.2 | 7.6 | 9.8 |
| $H_2$ | .3 | .5 | .7 | 1.0 | .4 | .6 | .9 | 1.6 |
| $CO/CO_2$ | 1.3 | .9 | .6 | .4 | .7 | .7 | .4 | .4 |
| $CH_4$ | 11.7 | 17.0 | 21.7 | 24.3 | 13.9 | 22.1 | 25.0 | 26.7 |
| $C_2H_6$ | 3.6 | 4.5 | 5.3 | 4.9 | 6.7 | 8.9 | 8.2 | 6.4 |
| $C_2H_4$ | 14.7 | 21.9 | 28.0 | 33.1 | 11.4 | 22.4 | 26.8 | 31.1 |
| $C_3H_8$ | SM | SM | SM | SM | SM | SM | SM | SM |
| $C_3H_6$ | 14.9 | 18.9 | 21.1 | 22.5 | 11.9 | 10.1 | 19.1 | 18.6 |
| $C_4H_{10}$ | 43.4 | 26.1 | 13.4 | 5.3 | 43.0 | 16.0 | 6.5 | 1.3 |
| $C_4H_8$ | 0 | 3.6 | 4.5 | 4.7 | 3.1 | 5.0 | 5.5 | 4.1 |
| Total | 100.0 | 100.0 | 100.0 | 100.0 | 100.0 | 100.0 | 100.0 | 100.0 |

What is claimed is:

1. A process for converting propane to ethylene, said process comprising contacting said propane with a catalyst comprising a crystalline aluminosilicate zeolite ZSM-50 having x-ray diffraction pattern as set forth in Table 1 under conditions sufficient to effect said propane to ethylene conversion.

2. A process according to claim 1, wherein said catalyst further comprises a binder for said ZSM-50.

3. A process according to claim 1, wherein said conversion conditions comprise a temperature of from about 100° C. to about 700° C., a pressure of from about 0.1 atmosphere to about 60 atmospheres, and a weighty hourly space velocity of from about 0.5 to about 400.

4. A process for converting propane to ethylene, said process comprising contacting said propane with a catalyst comprising a crystalline aluminosilicate zeolite ZSM-50 having x-ray diffraction pattern as set forth in Table 1 under conditions sufficient to effect said propane to ethylene conversion wherein an anhydrous acid oxide gas capable of accepting hydrogen by reacting therewith is also cofed with said propane for contact with said catalyst, the amount of said acidic oxide cofeed being sufficient to further increase the yield of ethylene produced from said propane.

5. A process according to claim 1, wherein said catalyst further comprises a binder for said ZSM-50.

6. A process according to claim 4, wherein said conversion conditions comprise a temperature of from about 100° C. to about 700° C., a pressure of from about 0.1 atmosphere to about 60 atmospheres, and a weight hourly space velocity of from about 0.5 to about 400.

7. A process according to claim 4, wherein said acidic oxide gas is sulfur dioxide.

* * * * *

UNITED STATES PATENT AND TRADEMARK OFFICE
CERTIFICATE OF CORRECTION

PATENT NO. : 4,929,791

DATED : May 29, 1990

INVENTOR(S) : Warren W. Kaeding

It is certified that error appears in the above-identified patent and that said Letters Patent is hereby corrected as shown below:

Column 1, line 40; "methanoI" should be --methanol--

Column 1, line 43; "majuor" should be --major--

Column 1, line 62; "foIIows" should be --follows--

Column 1, line 67; "ZSM50" should be --ZSM-50--

Column 2, line 35; "in" should be --In--

Column 2, line 42; "hasis" should be --basis--

Column 2, line 52; "$X(CH_3)_3N(CH_3)_3X$" should be --$X(CH_3)_3N(CH_2)_6N(CH_3)_3X$--

Column 3, line 52; "Plorida" should be --Florida--

Column 4, line 1; "90" should be --50--

Column 4, line 57; "Pive" should be --five--

Column 7, line 54; "weighty" should be --weight--

Column 8, line 50; "claim 1 " should be --claim 4--

Signed and Sealed this

Third Day of March, 1992

Attest:

HARRY F. MANBECK, JR.

*Attesting Officer*  *Commissioner of Patents and Trademarks*